United States Patent [19]

Fleischmann et al.

[11] Patent Number: 4,948,907

[45] Date of Patent: Aug. 14, 1990

[54] PROCESS FOR PREPARING LOW-MOLECULAR-WEIGHT ORGANO(POLY)SILOXANES

[75] Inventors: Gerald Fleischmann, Emmerting; Herbert Eck, Burghausen; Petra Wenzeler, Bubeureuth, all of Fed. Rep. of Germany

[73] Assignee: Wacker-Chemie GmbH, Munich, Fed. Rep. of Germany

[21] Appl. No.: 228,078

[22] Filed: Aug. 4, 1988

[30] Foreign Application Priority Data

Aug. 5, 1987 [DE] Fed. Rep. of Germany ....... 3726028

[51] Int. Cl.$^5$ ............................ C07F 7/08; C07F 7/10; C07F 7/18
[52] U.S. Cl. ..................................... 556/462; 556/413; 556/424; 556/425; 556/440; 556/451; 556/453; 556/457
[58] Field of Search ............... 556/413, 424, 425, 440, 556/451, 453, 457, 462

[56] References Cited

U.S. PATENT DOCUMENTS 3,337,497 8/1967 Bostich ........................... 556/457 X
3,481,965 12/1969 Selin ................................ 556/457 X

FOREIGN PATENT DOCUMENTS 0301067 11/1971 U.S.S.R. ............................... 556/453

*Primary Examiner*—Paul F. Shaver

[57] ABSTRACT

Linear low-molecular-weight organo(poly)siloxanes which are monofunctional or difunctional and in which, if difunctional, the two functionalities are present in siloxane units which are chemically different from each other are prepared by reacting an octaorganocyclotetrasiloxane with lithium silanolate in a molar ratio of 0.9:1 to 1.1:1 in an electron-donating, aprotic solvent at a temperature below 50° C., in the absence of water, and thereafter reacting the resultant lithium siloxanolate thus obtained with an organohalosilane.

7 Claims, No Drawings

PROCESS FOR PREPARING LOW-MOLECULAR-WEIGHT ORGANO(POLY)SILOXANES

The present invention relates to low-molecular-weight organo(poly)siloxanes, particularly to a process for preparing low-molecular-weight organo(poly)siloxanes from readily available cyclic diorganopolysiloxanes.

BACKGROUND OF THE INVENTION

Processes for preparing low-molecular-weight organo(poly)siloxanes which are straight-chain and monofunctional, i.e., for example, they have only one hydrogen atom bonded directly to a silicon atom per molecule or only one SiC-bonded, organofunctional group per molecule, by reacting a cyclic diorganopolysiloxane with a lithium silanolate in an electron-donating, aprotic solvent at a temperature below 50° C., and thereafter reacting the lithium siloxanolates thus prepared with an organohalosilane are described in Selin U.S. Pat. No. 3,481,965.

It is, therefore, an object of the present invention to provide a process for preparing low-molecular-weight organo(poly)siloxanes. Another object of the present invention is to provide a process for preparing linear monofunctional low-molecular-weight organo(poly)siloxanes. Still another object of the present invention is to provide a process for preparing linear difunctional low-molecular-weight organo(poly)siloxanes, in which the two functionalities are present in siloxane units which are chemically different from each other. A further object of the present invention is to provide a process for preparing low-molecular-weight organo(poly)siloxanes by reacting readily available cyclic diorganopolysiloxanes with relatively small amounts of a relatively inaccessible lithium compound.

SUMMARY OF THE INVENTION

The foregoing objects and others which will become apparent from the following description are accomplished in accordance with this invention, generally speaking, by providing a process for preparing linear low-molecular-weight organo(poly)siloxanes which are monofunctional or difunctional organo(poly)siloxanes, in which the two functionalities of the difunctional organo(poly)siloxanes are present in siloxane units which are chemically different from one another, which comprises reacting an octaorganocyclotetrasiloxane with a lithium silanolate in a molar ratio of octaorganocyclotetrasiloxane to lithium silanolate of 0.9:1 to 1.1:1 in an electron-donating, aprotic solvent at a temperature below 50° C., in the absence of water, and thereafter reacting the lithium siloxanolates thus obtained with an organohalosilane.

DESCRIPTION OF THE INVENTION

Applicants' process for preparing low-molecular-weight organo(poly)siloxanes is very surprising in view of the teachings of Bostick U.S. Pat. No. 3,337,497, which discloses at column 3, lines 50 to 64, that if an octaorganocyclotetrasiloxane, for example, octamethylcyclotetrasiloxane, is employed initially with an organolithium compound in place of a hexaorganocyclotrisiloxane, e.g. hexamethyltrisiloxane, little if any reaction occurs under the prescribed conditions, especially at temperatures below 100° C.

In contrast to the teachings of U.S. Pat. No. 3,337,497, applicants have found that a reaction does in fact occur at temperatures below 100° C.

The octaorganocyclotetrasiloxanes employed in the process of this invention can be represented by the formula

$(R_2SiO)_4$ where R represents the same or different monovalent hydrocarbon radicals which are free of aliphatic multiple bonds.

The SiC-bonded organic radicals in the organosilicon compounds employed in the process of this invention, which are represented by R, $R^1$ and $R^2$ radicals in the formulas, preferably contain a maximum of 18 carbon atoms per radical. Examples of such R radicals are alkyl radicals, such as the methyl, ethyl, n-propyl, isopropyl, n-butyl, sec-butyl and octadecyl radicals; cycloalkyl radicals, such as the cyclohexyl and methylcyclohexyl radicals; aryl radicals, such as the phenyl and xenyl radicals; alkaryl radicals, such as the tolyl radicals; and aralkyl radicals, such as the benzyl radical.

Due to its availability, the preferred cyclic tetrasiloxane is octamethylcyclotetrasiloxane.

The lithium silanolates preferably employed in the process of this invention are represented by the formula

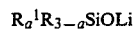

$R_a^1R_{3-a}SiOLi$ in which R is the same as above, $R^1$ is a monovalent hydrocarbon radical containing an aliphatic double bond, and a is 0 or 1. Examples of $R^1$ radicals are alkenyl radicals, such as the vinyl and allyl radicals, and cycloalkenyl radicals, such as cyclohexenyl and methylcyclohexenyl radicals.

Preferred lithium silanolates are those of the formula

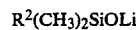

$R^2(CH_3)_2SiOLi$ in which $R^2$ is an alkyl radical having from 2 to 18 carbon atoms per radical, preferably a butyl radical, and more preferably the n-butyl radical, even though the ethyl radical may be employed.

However, lithium silanolates which can be used in the process of this invention may also be, for example, lithium trimethylsilanolate, lithium triethylsilanolate, lithium tris(2-ethylhexyl)silanolate, lithium triphenylsilanolate, lithium dimethylvinylsilanolate and lithium methyldiphenylsilanolate.

Electron-donating, aprotic solvents which can be used in the process of this invention are aprotic solvents which have an unshared electron pair in the molecule and in which it has heretofore been possible to carry out the reaction of a cyclic diorganopolysiloxane with a lithium silanolate. Tetrahydrofuran is particularly preferred as an aprotic solvent.

The amount of electron-donating, aprotic solvent employed can also be the same in the process of this invention as has been or could have been employed heretofore in the reaction of a cyclic diorganopolysiloxane with a lithium silanolate in an electron-donating, aprotic solvent. This amount is preferably from 2 to 50 parts by weight per part by weight of the total amount of the organosilicon compounds employed.

The reaction of the octaorganocyclotetrasiloxane with a lithium silanolate is preferably carried out at 0° to 25° C. and more preferably from 19° to 21° C.. Higher temperatures favor the formation of undesired by-products, and lower temperatures produce undesirably low space-time yields.

The terms "in the absence of water" or "with the exclusion of water" as used herein means that the reactants and the solvents are free of water exceeding 1 part by weight per million parts by weight of the total weight of the reactants and solvents and that the mixture of octaorganocyclotetrasiloxane, lithium silanolate and solvent and finally the product produced in the reaction is excluded from water. The solvent can be freed from water in a known manner, for example, by distillation over, for example, a sodium/potassium alloy or sodium hydride or adsorptive drying by means of, for example, activated aluminum oxide (specific BET surface area: 300 to 350 m²/g). The use of sublimed lithium silanolate, such as described in U.S. Patent No. 3,481,965, mentioned heretofore, is not necessary in the process of this invention and preferably is not carried out in accordance with the patent.

The duration of the reaction of the octaorganocyclotetrasiloxane with a lithium silanolate is preferably from 12 to 72 hours.

The reaction of the octaorganocyclotetrasiloxane with a lithium silanolate can be represented by the equation $$(R_2SiO)_4 + R_a{}^1R_{3-a}SiOLi \rightarrow R_a{}^1R_{3-a}SiO(R_2SiO)_nLi$$

where R and $R^1$ are the same as above, a is 1, 2, 3 or 4, and n is 1, 2, 3 or 4.

The organohalosilanes employed in the second step of the process of this invention are preferably those having the formula $$XSiR^3R_2$$

in which R is the same as above and $R^3$ represents hydrogen, halogen, an alkoxy group having from 1 to 5 carbon atoms or a hydrocarbon radical having a maximum of 18 carbon atoms and contains an aliphatic multiple bond or a hydrocarbon radical which has a maximum of 18 carbon atoms and is free of aliphatic multiple bonds and contains a substituent which is inert towards the reactants, and X represents chlorine, bromine or iodine, preferably chlorine, with the proviso that the hydrocarbon radicals represented by $R^3$ containing an aliphatic multiple bond must be different from the $R^1$ radicals of this type.

Examples of hydrocarbon radicals represented by $R^3$ containing an aliphatic multiple bond are the vinyl, allyl, cyclohexenyl and styryl radicals.

Examples of hydrocarbon radicals represented by $R^3$ containing a substituent which is inert towards the reactants are acyloxyalkyl radicals, such as the gamma-acryloxypropyl and gamma-methacryloxypropyl radicals, and also radicals containing basic nitrogen, such as those of the formula $$H_2N(CH_2)_2NH(CH_2)_3- \text{ and cyclohexyl} -NH(CH_2)_3-.$$

The organohalosilane used in the second step of the process of this invention is preferably employed in an amount of at least 1.02 moles, and more preferably in an amount of 1.05 moles, per gram-atom of lithium.

The second step of the process of this invention is preferably carried out without first isolating the lithium siloxanolates obtained in the first step.

The reaction of the lithium siloxanolates with an organohalosilane is preferably carried out at a temperature below about 50° C. in the absence of water.

The reaction of lithium siloxanolates obtained in the first step of the process of this invention with the organohalosilane can be represented by the equation $$R_a{}^1R_{3-a}SiO(SiR^2{}_2O)_nLi + XSiR^2R_2 \rightarrow R_a{}^1R_{3-a}SiO(SiR^2O)_nSiR^2R_2 + LiX$$

in which R, $R^1$, $R^2$, X, a and n are the same as above.

Both steps of the process of this invention are preferably carried out at the pressure of the ambient atmosphere, i.e., at 1020 hPa (abs.) or at about 1020 hPa (abs.) If desired, however, higher or lower pressures can also be used.

The low-molecular-weight organo(poly)siloxanes prepared according to this invention can be used where such products are desired. In particular, when they contain aliphatic multiple bonds, then homopolymers or copolymers, for example, can be prepared from them, which may be used, for example, to form gas-permeable membranes or contact lenses. In addition, the organopolysiloxanes prepared according to this invention can, for example, be used as plasticizers for polymers or as starting materials for such plasticizers and as starting materials for emulsifiers.

The lithium silanolate of the formula $$n-C_4H_9(CH_3)_2SiOLi$$

used in some of the following examples was prepared as follows:

About 125 mmol of n-butyllithium (50 ml of a 2.5 molar solution of n-butyllithium in n-hexane) are added dropwise under dry argon with exclusion of water to a stirred solution containing 31.25 mmol (9.27 g) of octamethylcyclotetrasiloxane, distilled over calcium hydride, in 200 ml of tetrahydrofuran which has been distilled over sodium hydride, with external cooling of the reaction vessel, so that the temperature of the contents of the vessel does not exceed 20° C. The mixture is subsequently stirred for an additional 3 hours at 20° C. under argon with exclusion of water.

EXAMPLE 1

(a) About 125 mmol (37.08 g) of octamethylcyclotetrasiloxane which has been distilled over calcium hydride are added dropwise under dry argon with exclusion of water to the stirred lithium n-butyldimethylsilanolate solution whose preparation is described above, with external cooling of the reaction vessel, so that the temperature of the contents of the vessel does not exceed 20° C. The mixture is subsequently stirred for an additional 18 hours at 20° C. under argon with the exclusion of water.

(b) About 130 mmol (17.65 g) of vinyldimethylchlorosilane are added dropwise under dry argon with exclusion of water to the stirred solution of lithium siloxanolates whose preparation is described in Example 1(a) above with external cooling of the reaction vessel so that the temperature of the contents of the vessel does not exceed 20° C. After stirring the mixture for 10 hours at 20° C., the tetrahydrofuran is removed by distillation, the lithium chloride is filtered off and the filtrate is fractionated at 0.1 Pa (abs.).

The fractions are identified by means of gel chromatography, mass spectroscopy, the $^1$H nuclear magnetic resonance spectrum and the $^{29}$Si nuclear magnetic resonance spectrum. The results are shown in Table 1.

TABLE 1

| Fraction | b.p. °C. | at (abs.) | Proportion % by weight | Yield, based on unreacted tetrasiloxane % by weight of theory |
|---|---|---|---|---|
| BuSi(CH$_3$)$_2$OSi(CH$_3$)$_2$CH=CH$_2$ | 92–93 | 2 hPa | 21.33 | 45.8 |
| Bu[Si(CH$_3$)$_2$O]$_3$Si(CH$_3$)$_2$CH=CH$_2$ | 62 | 10 Pa | 3.2 | 6.80 |
| Bu[Si(CH$_3$)$_2$O]$_4$Si(CH$_3$)$_2$CH=CH$_2$ | 77–79 | 10 Pa | 4.92 | 10.23 |
| Bu[Si(CH$_3$)$_2$O]$_5$Si(CH$_3$)$_2$CH=CH$_2$ | 91–93 | 10 Pa | 16.83 | 35.74 |
| [Si(CH$_3$)$_2$O]$_4$ | 65–67 | 2 hPa | 52.91 | — |
| Not identified. | — | | 1 | — |

Bu = n-C$_4$H$_9$

EXAMPLE 2

The procedure described in example 1 (a) and (b) is repeated, except that the temperature is 0° C. instead of 20° C. during addition of the octamethylcyclotetrasiloxane and during the subsequent stirring.

The fractions obtained on distillation at 0.1 Pa (abs.) are identified as specified in example 1. The results are shown in Table 2.

TABLE 2

| Fraction | Proportion % by weight | Yield, based on unreacted tetrasiloxane % by weight of theory |
|---|---|---|
| BuSi(CH$_3$)$_2$OSi(CH$_3$)$_2$CH=CH$_2$ | 30.47 | 79.68 |
| BuSi[(CH$_3$)$_2$O]$_3$Si(CH$_3$)$_2$CH=CH$_2$ | 1.52 | 3.98 |
| Bu[Si(CH$_3$)$_2$O]$_4$Si(CH$_3$)$_2$CH=CH$_2$ | 1.69 | 4.42 |
| Bu[Si(CH$_3$)$_2$O]$_5$Si(CH$_3$)$_2$CH=CH$_2$ | 4.55 | 11.90 |
| [Si(CH$_3$)$_2$O]$_4$ | 61.76 | |

Bu = n-C$_4$H$_9$

EXAMPLE 3

The procedure described in Example 1 (a) and (b) is repeated, except that the mixture is stirred for 72 hours at 20° C. instead of for 18 hours at 20° C. after addition of the octamethylcyclotetrasiloxane, and only the hexaorganodisiloxane and the octamethylcyclotetrasiloxane are removed by distillation from the filtrate obtained on filtering off the lithium chloride. The yield of siloxane of the formula n—C$_4$H$_9$Si(CH$_3$)$_2$OSi(CH$_3$)$_2$CH=CH$_2$ in a purity of at least 95 percent by weight is 71 percent by weight, based on the reacted tetrasiloxane.

EXAMPLE 4

(a) The procedure described in example 1 (a) is repeated, except that the mixture is stirred for 42 hours at 20° C. instead of for 18 hours after addition of the octamethylcyclotetrasiloxane.

(b) About 188 mmol (20.5 g) of dimethylchlorosilane are added dropwise under dry argon with exclusion of water to the stirred solution of a lithium siloxanolate whose preparation is described in Example 4(a) above, with external cooling of the reaction vessel so that the temperature of the contents of the vessel does not exceed 20° C. After the mixture has been stirred at 20° C. for 2 hours, the tetrahydrofuran is removed by distillation, the lithium chloride is filtered off and the filtrate is distilled at 15 to 0.1 Pa (abs.). The fractions thus obtained are identified as specified in example 1. The results are shown in Table 3.

TABLE 3

| Fraction | b.p. °C. | Proportion % by weight | Yield, based on unreacted tetrasiloxane % by weight of theory |
|---|---|---|---|
| BuSi(CH$_3$)$_2$OSi(CH$_3$)$_2$H | 48[1] | 11.81 | 20.12 |
| Bu[Si(CH$_3$)$_2$O]$_3$Si(CH$_3$)$_2$H | 90[1] | 3.31 | 5.64 |
| Bu[Si(CH$_3$)$_2$O]$_4$Si(CH$_3$)$_2$H | 68–70[2] | 8.30 | 14.14 |
| Bu[Si(CH$_3$)$_2$O]$_5$Si(CH$_3$)$_2$H | 85–86[3] | 28.00 | 47.49 |
| [Si(CH$_3$)$_2$O]$_4$ | | 41.29 | — |
| Not identified.[4] | | 7.28 | — |

Bu = n-C$_4$H$_9$
[1] = at 2 hPa (abs.).
[2] = at 10 Pa (abs.).
[3] = at 20 Pa (abs.).
[4] = higher molecular weight; may be attributable to the fact that the dimethylchlorosilane may be contaminated with methyldichlorosilane.

EXAMPLE 5

(a) About 128 mmol of methyllithium (80 ml of a 1.6 molar solution of methyllithium in diethyl ether) are added dropwise under dry argon with exclusion of water to a stirred solution containing 32 mmol (9.5 g) of octamethylcyclotetrasiloxane which has been distilled over calcium hydride, in 150 ml of tetrahydrofuran which has been distilled over sodium hydride. The contents of the reaction vessel are subsequently warmed to reflux.

(b) About 128 mmol (38 g) of octamethylcyclotetrasiloxane which has been distilled over calcium hydride are added dropwise under argon with exclusion of water to the stirred lithium trimethylsilanolate solution whose preparation is described in Example 5 (a) above, after cooling to 15° C., with external cooling of the reaction vessel so that the temperature of the contents of the vessel does not exceed 20° C. The mixture is subsequently stirred for 48 hours under argon with exclusion of water.

(c) About 140 mmol (16.6 g) of vinyldimethylchlorosilane are added dropwise under dry argon with exclusion of water to the stirred solution of a lithium siloxanolate whose preparation is described in Example 5 (b) above, with external cooling of the reaction vessel so that the temperature of the contents of the vessel does not exceed 20° C. After the mixture has been stirred at 20° C. for 6 hours, the tetrahydrofuran is removed by distillation, the lithium chloride is filtered off and the filtrate is fractionated at the pressure of the ambient atmosphere to 15 Pa (abs.). The results are shown in Table 4.

TABLE 4

| Fraction | b.p. °C. | Proportion % by weight | Yield, based on unreacted tetrasiloxane % by weight of theory |
|---|---|---|---|
| $CH_3Si(CH_3)_2OSi(CH_3)_2CH=CH_2$ | 120–122[1] | 8.32 | 15.27 |
| $CH_3[Si(CH_3)_2O]_3Si(CH_3)_2CH=CH_2$ | 92[2] | 7.28 | 13.36 |
| $CH_2[Si(CH_3)_2O]_4Si(CH_3)_2CH=CH_2$ | 110–111[2] | 14.83 | 27.22 |
| $CH_2[Si(CH_3)_2O]_5Si(CH_3)_2CH=CH_2$ | 135[2] | 22.51 | 41.32 |
| $[Si(CH_3)_2O]_4$ | | 45.52 | — |
| Not identified. | | 1.52 | — |

[1]At about 1000 hPa (abs.).
[2]At 2 hPa (abs.).

What is claimed is:

1. A process for preparing linear low-molecular weight organo(poly)siloxanes, having one or two functional groups which are bonded to siloxane units wherein not more than one functional group is bonded to one siloxane unit, which comprises reacting an octaorganocyclotetrasiloxane with a lithium silanolate in a molar ratio of octaorganocyclotetrasiloxane to lithium silanolate of from 0.9:1 to 1.1:1 in an electron-donating, aprotic solvent at a temperature below 50° C., in the absence of water, and thereafter reacting the resultant lithium siloxanolate thus obtained with an organohalosilane.

2. The process of claim 1, wherein the octaorganocyclotetrasiloxane is octamethylcyclotetrasiloxane.

3. The process of claim 1, wherein the lithium silanolate has the formula n—$C_4H_9(CH_3)_2SiOLi$.

4. The process of claim 2, wherein the lithium silanolate has the formula n—$C_4H_9(CH_3)_2SiOLi$.

5. The process of claim 1, wherein the reaction of the octaorganocyclotetrasiloxane with a lithium silanolate is carried out at a maximum temperature of 22° C.

6. The process of claim 5, wherein the octaorganocyclotetrasiloxane is octamethylcyclotetrasiloxane.

7. The process of claim 5, wherein the lithium silanolate has the formula n—$C_4H_9(CH_3)_2SiOLi$.

* * * * *